United States Patent
Liu et al.

(10) Patent No.: US 11,534,234 B2
(45) Date of Patent: Dec. 27, 2022

(54) METHOD AND DEVICE FOR INTERVENTRICULAR SEPTAL ABLATION

(71) Applicant: Fourth Military Medical University, Shaanxi (CN)

(72) Inventors: Liwen Liu, Shaanxi (CN); Rui Hu, Shaanxi (CN)

(73) Assignee: Fourth Military Medical University, Shaanxi (CN)

( * ) Notice: Subject to any disclaimer, the term of this patent is extended or adjusted under 35 U.S.C. 154(b) by 768 days.

(21) Appl. No.: 16/493,273

(22) PCT Filed: Jan. 2, 2018

(86) PCT No.: PCT/CN2018/070054
§ 371 (c)(1),
(2) Date: Sep. 11, 2019

(87) PCT Pub. No.: WO2018/127039
PCT Pub. Date: Jul. 12, 2018

(65) Prior Publication Data
US 2020/0030022 A1  Jan. 30, 2020

(30) Foreign Application Priority Data

Jan. 6, 2017  (CN) .......... 201710009526.X
Aug. 29, 2017  (CN) .......... 201710756752.4

(51) Int. Cl.
*A61B 18/12* (2006.01)
*A61B 18/14* (2006.01)
(Continued)

(52) U.S. Cl.
CPC ........ *A61B 18/1477* (2013.01); *A61B 5/0006* (2013.01); *A61F 2/0105* (2020.05);
(Continued)

(58) Field of Classification Search
CPC .......... A61B 2018/00577; A61B 2018/00351; A61B 18/1477; A61F 2/011
See application file for complete search history.

(56) References Cited

U.S. PATENT DOCUMENTS 7,947,040 B2 * 5/2011 Davies ............... A61B 18/1492
606/41
2003/0032936 A1 * 2/2003 Lederman .......... A61B 18/1492
604/164.09
(Continued)

FOREIGN PATENT DOCUMENTS

CN   103385770 A   11/2013

OTHER PUBLICATIONS

WIPO, International Preliminary Examining Authority (The International Bureau of WIPO), International Preliminary Report on Patentability dated Jul. 9, 2019 in International Patent Application No. PCT/CN2018/070054, 5 pages.
(Continued)

*Primary Examiner* — Daniel W Fowler
(74) *Attorney, Agent, or Firm* — Inskeep IP Group, Inc.

(57) ABSTRACT

A method for treating hypertrophic cardiomyopathy (HCM) utilizes an RF ablation electrode needle system that has an RF ablation generator, and an electrode needle. The electrode needle is introduced to puncture within myocardium and to reach the hypertrophic area of the interventricular septum. The RF ablation generator is then turned on to implement single-point or multi-point ablation on the hypertrophic area of the interventricular septum, and then the RF electrode needle is withdrawn from the patient.

29 Claims, 15 Drawing Sheets

(51) Int. Cl.
 *A61B 5/00* (2006.01)
 *A61F 2/01* (2006.01)
 *A61B 18/00* (2006.01)
(52) U.S. Cl.
 CPC .............. *A61B 2018/00351* (2013.01); *A61B 2018/00577* (2013.01); *A61F 2/011* (2020.05)

(56) References Cited

U.S. PATENT DOCUMENTS

2009/0093803 A1* 4/2009 Herrin ................ A61B 18/1492
 606/50
2013/0310823 A1* 11/2013 Gelfand ................ A61B 18/18
 606/41
2017/0258521 A1* 9/2017 Asirvatham ....... A61B 18/1492

OTHER PUBLICATIONS

WIPO, International Search Authority (State Intellectual Property Office of the P.R. China), Declaration of Non-establishment of International Search Report and Written Opinion dated Mar. 29, 2018 in International Patent Application No. PCT/CN2018/070054, 4 pages.

* cited by examiner

Cross sectional view

METHOD AND DEVICE FOR INTERVENTRICULAR SEPTAL ABLATION

RELATED APPLICATIONS

This application is the U.S. National Phase of and claims priority to International Patent Application No. PCT/CN2018/070054, International Filing Date Jan. 2, 2018, entitled Method And Device For Interventricular Septal Ablation; which claims benefit of Chinese Application No. 201710009526.X filed Jan. 6, 2017; and Chinese Application No. 201710756752.4 filed Aug. 29, 2017; all of which are incorporated herein by reference in their entireties.

TECHNICAL FIELD

The present invention relates to the treatment of hypertrophic cardiomyopathy (HCM), and in particular, to methods and devices for carrying out interventricular septal ablation to treat HCM. The present invention treats HCM through the use of percutaneous intramyocardial septal radiofrequency ablation (RFA).

DESCRIPTION OF THE PRIOR ART

HCM is one of the most common genetic cardiovascular disorders inherited as an autosomal dominant trait in the traditional sense, with an occurrence of 1:500 and a mortality of 1.4%-2.2% in the general population, and with a sudden death incidence of up to 5.9% in the high-risk population, namely groups having non-sustained ventricular tachycardia (NSVT), syncope and a family history of sudden death. The natural clinical history of HCM varies considerably. Some patients show no obvious clinical symptoms, but it can also lead to severe consequences such as chest distress, chest pain, dyspnea, recurrent syncope, atrial fibrillation, ventricular tachycardia, heart failure, or even sudden death. HCM is considered as the most common cause of sudden death in youngsters and athletes.

HCM is mainly characterized by hypertrophy in one or more segments of the left ventricle (LV), and generally its diagnostic criteria are defined by a wall thickness ≥15 mm. When the presence of systolic anterior motion (SAM) of the anterior mitral leaflet and attachment to the ventricular septum results in narrowing or even obstruction of left ventricular outflow tract (LVOT), namely very high LVOT pressure gradient (PG), this symptom is called Hypertrophic Obstructive Cardiomyopathy (HOCM), accounting for 70% of all HCM patients. Consequently, treatment strategies against HOCM are directed at enlarging the LVOT, thereby reducing PG and relieving the LVOT obstruction. This is mentioned in the 2014 European Society of Cardiology (ESC) Guidelines on the diagnosis and management of hypertrophic cardiomyopathy, published by the ESC in 2014.

Treatment methods mainly include medications, alcohol septal myocardial ablation, and modified ventricular septal hypertrophic myocardium myectomy (also known as surgical myectomy or Modified Morrow Procedure). So far, the Modified Morrow Procedure has become a highly mature therapeutical procedure, and surgical myectomy has been advocated as the gold standard for the treatment of HCM by expert consensus. Two articles provide a comparison between surgical myectomy and alcohol septal ablation: *Comparison of Surgical Septal Myectomy and Alcohol Septal Ablation With Cardiac Magnetic Resonance Imaging in Patients With Hypertrophic Obstructive Cardiomyopathy*, Valeti et al., Journal of the American College of Cardiology, Vol. 49, No. 3, 2007, and *Comparison of ethanol septal reduction therapy with surgical myectomy for the treatment of hypertrophic obstructive cardiomyopathy*, Nagueh et al., Journal of the American College of Cardiology, Vol. 38, No. 6, 2001.

Recently, another approach has been suggested in *Echocardiography-guided per-cutaneous per-ventricular laser ablation of ventricular septum: in vivo study in a canine model*, He et al., Lasers in Medical Science, 2016, which uses ultrasound-guided transapical septal radio frequency ablation for hypertrophic cardiomyopathy. Under the guidance of a color doppler ultrasound instrument, pre-puncture positioning is carried out by using a cardiac probe in a long-axis or short-axis session guide line mode. A radio frequency electrode needle is then fixed to a multi-angle puncture trestle or support structure (hereinafter referred to as "trestle") introduced via a transthoracic intercostal route, and passed through the skin, subcutaneous tissue, and pericardium to reach the pre-ablation site. The electrode needle is inserted into the right ventricle with its tip reaching the targeted basal to mid-septum. The angle of insertion against the septum a was approximately less than 45°. The needle insertion process is monitored in real time by means of ultrasound. Then, fixed-power radio frequency ablation is carried out for a period of time to achieve the desired ablation.

Unfortunately, this procedure described by He et al. has some drawbacks. First, there are many conduction bundles distributed on the wall of the left ventricle (LV) and right ventricle (RV), so when the needle is inserted into the RV, it will contact the conduction bundles which could result in cardiac arrhythmia. In addition, the needle will contact with the blood in the RV, which may result in the formation of thrombus.

There are additional problems associated with the needle insertion procedure described by He et al. For example, during this procedure, the site of septal hypertrophy varies with different HCM patients, and even for a same patient, the extent of hypertrophy also varies significantly among the basal, mid and apical parts of the septum. In addition, clinical treatment also requires the electrode needle to provide direct drug injection or water cooling at the ablation site. Therefore, there is a need for a multifunctional RFA electrode needle having both an electrode exposure length adjusting function, and a drug injection function that can also be used for cooling of ablated tissue, so as to adapt to complex multi-ablation environments having high requirements on the range of ablation, so as to achieve precise treatment.

Currently, radio frequency electrode needles applied clinically only have a limited function. Most of these electrode needles have a fixed exposure length and do not have a drug injection function. One of the available conventional adjustable electrode needles is an adjustable radio frequency ablation electrode needle invented by Zhuhai Hokai Medical Instruments Co., Ltd., which, though allowing the adjustment of the exposure length of the tip, does not have a drug injection function.

As can be seen, the conventional radio frequency electrode needles are insufficient for use in ultrasound-guided intramyocardial septal radio frequency ablation for HCM. Therefore, there is a need for a multifunctional radio frequency ablation electrode needle, and in particular, a radio frequency ablation electrode needle having both a drug injection function and an electrode exposure length adjusting function.

Another problem associated with the needle insertion procedure described by He et al. is the flow of debris from the ablation. To prevent the possible formation of thrombus, embolus or other tissue debris during the radio frequency ablation or a period of time after the radio frequency ablation, and especially to prevent left ventricular thrombus, embolus or other tissue debris from flowing into the aorta along with the blood flow to cause severe complications such as cerebral embolism and other tissue embolism during the ablation of the septal myocardium or left ventricular tumor, there is a need for an artery filter assembly that can be placed in an aorta to filter thrombus, embolus or other tissue debris in a screen form without diminishing the blood flow in the aorta, so as to prevent embolic complications.

Currently, among clinically applied vascular filters, there are only a few artery filters, and most of them are vena cava filters. Vena cava filters include permanent and non-permanent filters. Permanent filters are more widely used. The permanent filter is permanently fixed on the vascular wall. However, because it will remain in the human body long term as a foreign object, the patient needs to take anticoagulants throughout his/her life, and may suffer from complications such as displacement, piecing or local thrombosis. Non-permanent filters are retrievable filters that can be retrieved from the human body after a period of time, and therefore can avoid the problems such as the complications caused by permanent filters. However, angiosynizesis makes it difficult to retrieve the filter. In addition, conventional artery filters have been applied to lesions on the aortic arch and can prevent cerebral embolism. However, they are also difficult to retrieve, and the thrombus may overflow or break.

Thus, the conventional vascular filters cannot be used to address the existing problems for the treatment of HCM. Therefore, there is a need for a novel vascular filter, and in particular, a retrievable vascular filter assembly that is adapted to be placed in an aorta and is capable of filtering thrombus, embolus or other tissue debris.

SUMMARY OF THE DISCLOSURE

In order to accomplish the objects of the present invention, there is provided a method for treating hypertrophic cardiomyopathy (HCM). According to this method, an RF ablation electrode needle system is provided comprising an RF ablation generator, imaging equipment for displaying the myocardium, and an electrode needle. The electrode needle is introduced to puncture the ventricular septum myocardium and to reach the hypertrophic area of the ventricular septum along a long axis of the septum. The RF ablation generator is then turned on to implement single-point or multi-point ablation on the hypertrophic area of the ventricular septum, and then the RF electrode needle is withdrawn from the patient. During the procedure, the electrode needle is prevented from contacting conduction bundles at the endocardia during the puncture process.

As part of this procedure, after ablation is performed at a first ablation site, the electrode needle is withdrawn by a predetermined distance to a second ablation site for ablation for a second predetermined period of time, and this can be repeated for a plurality of additional ablation sites.

According to one embodiment of the present invention, the electrode needle can be introduced into another position of the hypertrophic area of the ventricular septum along a later puncture pathway after ablation has been performed on a preceding puncture pathway without the electrode needle being withdrawn out of the epicardium of the apex.

DESCRIPTION OF EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices and mechanisms are omitted so as to not obscure the description of the present invention with unnecessary detail.

As used herein, the term "apical portion" is defined as the apical portion of the left ventricle, where there is a bare area without a coronary artery covering it.

The term "apical area in the direction to which interventricular septum extends" is referred to as "apical portion of the interventricular septum" for convenience hereinafter.

The term "the connection part of apex and septum" refers to a junction of the interventricular septum and the apex.
Treatment Method of the Present Invention As shown in FIGS. 1 through 16, the treatment method for HCM according to the present invention is an ultra-minimally invasive treatment method with using an electrode needle. The electrode needle punctures into the heart interventricular septum through percutaneous intercostal, the epicardium, the apical portion of the interventricular septum 256, and the connection part of apex and septum 257, to destroy the myocardial viability of the thickened interventricular septum 253 by means of ablation. The electrode needle is powered to produce RF current, with which the myocardium of the interventricular septum 253 is ablated. The electrode needle releases heat to the lesion interventricular septum 253 to destroy its viability so as to cause protein degeneration and apoptosis at the target myocardial, decreasing a moving amplitude of the interventricular septum 253 instantly, and eventually resulting in myocardial fibrosis gradually and thereby thinning the interventricular septum 253. In the treatment method of the present invention, the treatment needle punctures into the interventricular septum 253 to ablate the hypertrophic ventricular septum 253, thereby causing protein denaturation and cell necrosis or apoptosis at the hypertrophic ventricular septum 253, and eventually cause thinning of the myocardial and myocardial fibrosis.

Figure 1:
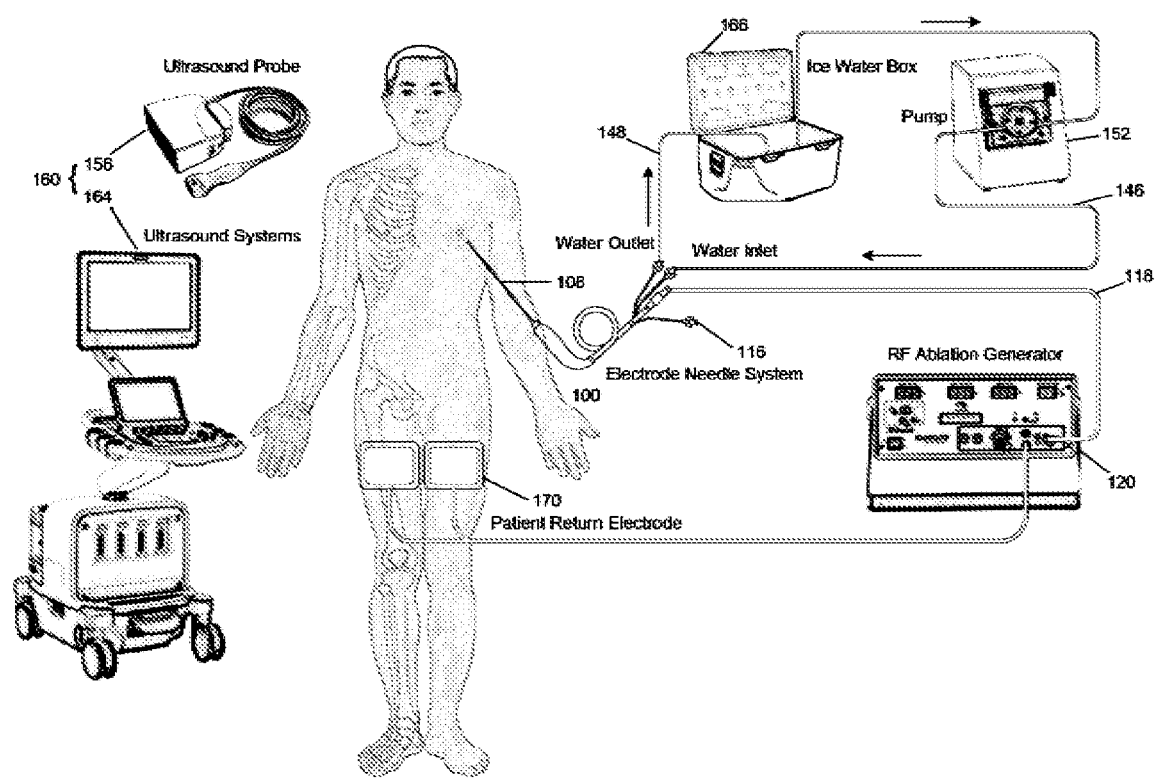
FIG. 1 is a system diagram illustrating the major components of a system for performing interventricular septal ablation to treat HCM under the present invention.

It can be understood that the needle used for puncturing into the interventricular septum 253 can also be a therapeutic needle which is capable of transmitting energy and/or medicine to destroy the myocardial viability of the interventricular septum 253, The energy transmitted by the therapeutic needle can be one of: heat, cold, light, electricity, gas, mechanical waves, electromagnetic waves, radioactive particles, or any combination thereof, The energy generating device can be a generator of energy in the form of: radio frequency, microwave, laser, or focused ultrasonic, which is capable of heating the local tissue to increase the temperature thereof. Alternatively, the energy generating device can also be an argon-helium supercooling knife or a radioactive particle implantation device, which is capable of lowering down the temperature of the local tissue, Correspondingly, the therapeutic needle can be a radio frequency electrode needle, a microwave ablation needle, a laser fiber, an ultrasound transducer, an argon-helium knife, or a particle implantation catheter. Alternatively, the therapeutic needle may be used with a combination of energy and medicine. The target area can be pretreated with medicine before the needle releasing energy so as to speed up the treatment or minimize the harm to the human body when the energy is released. It is also possible that medicine is released to the treatment area after the treatment of the needles with energy, to minimize the risk of surgical complications and to facilitate healing.
System FIG. 1 illustrates a system according to the present invention for performing interventricular septal ablation to treat HCM. The system includes a multifunctional radio frequency (RF) ablation electrode needle system 100 having an RF electrode needle 108, an RF ablation generator 120, an ultrasound system 160 that includes an ultrasound probe 156 and a conventional ECG monitoring and ultrasound machine 164, and a water pump 152.

The RF ablation electrode needle system 100 is described in greater detail below and functions primarily to perform the ventricular septal ablation according to the procedure described hereinbelow. The water outlet 148 for the needle system 100 is coupled to an ice water box 166 which is in turn coupled to the pump 152. The water inlet 146 for the needle system 100 is coupled to the outlet of the pump 152.

A radio frequency power line 118 extends from the needle system 100 to an RF ablation generator 120. A pair of patient return electrodes 170 is positioned on the two thighs of the patient and is in turn coupled to the RF ablation generator 120. The RF signal from the RF ablation generator 120 is a current, and it works only when a current loop is formed. During the ablation treatment, the electrode needle 108 (see FIG. 7) acts as the positive electrode, and the two patient return electrodes act as the negative electrode, which cooperate to form a current loop flowing through the body of the patient.

The RF ablation generator 120 supplies a power level ranging between 30 W and 150 W for each of the single-point or multi-point ablations. In one embodiment, the power level is in the range of 60 W to 120 W, and is preferably 80 W in another embodiment.

The ultrasound system 160 functions to provide imaging for the procedure described below.
Procedure The system of FIG. 1 can be used to apply the following procedure for performing ventricular septal ablation to treat HCM.

Before the procedure, pre-operative preparations are taken. Specifically, preoperative conversations between the doctors and patient are conducted to arrange for the procedure.

Next, certain tests are conducted to determine if the procedure can be done on the patient. For example, the following tests can be conducted: a myocardial injury examination, ECG, Holter, Cardiac Magnetic Resonance (CMR), Echocardiography, stress echo test, coronary artery CT angiography (CTA), and other routine preoperative examinations. Myocardial injury examination can include troponin I (TropI), myoglobin (Mb), creatine kinase isoenzyme mass (CK-MB mass), and B-type brain natriuretic peptide (Pro-BNP), and used for the purpose of clarifying the extent of myocardial injury in patients. ECG (routine electrocardiogram) and Holter (24-hour dynamic electrocardiogram) tests are performed for the purpose of clarifying cardiac electrophysiology activities and the presence or absence of arrhythmia in patients, and simultaneously the presence or absence of NSVT reflected from Holter is an important indication to evaluate sudden cardiac death index (SCDI). Echocardiography is a preferred choice for an imaging technique for diagnosis of HCM to clarify the patient's cardiac function, ventricular wall thickness, LVOT PG, etc., and to decide whether the patient has outflow tract obstruction. CMR is performed for the purpose of clarifying ventricular wall thickness, and the degree and position of myocardial fibrosis. Stress echo test is performed for the purpose of clarifying the presence or absence of potential obstruction in patients. CTA is performed for the purpose of clarifying the presence or absence of lesions in the coronary artery, and simultaneously understanding the coronary geometry to avoid damage to the coronary artery during the puncture process. There are also routine preoperative examinations, such as general examinations when admitted to hospital and before the procedure, which can be used for screening for other accompanying diseases.

In the next step, a preliminary determination of the optimal needle pathway is made. The main factors that need to be considered when deciding the needle pathway include: (i) avoiding intercostal arteries and veins, apical coronary arteries and veins when inserting the needle; (ii) for patients having complications associated with apical ventricular aneurysm, avoiding damage to the ventricular aneurysm; and (iii) keeping the direction of needle insertion parallel to the long axis of the ventricular septum. In this regard, it is important to identify the apical position and coronary vascular distribution, and then simulating the needle pathway on the basis of three-dimensional models of the heart and ventricular septum during the preoperative planning.

Then, the target ablation area is determined by determining the size of the obstruction zone based on the area of LVOT obstruction and/or left ventricular intracardiac obstruction in the apical four or five chamber view and the left ventricular short axis view. This attempts to compose three-dimensional image results in the operators' mind according to plane length data from two-dimensional ultrasound. Specifically, in the preoperative planning system, the hypertrophic ventricular septum is marked on the three-dimensional models of the heart used as the target ablation area, according to indexes such as interventricular septal thickness (IVST). Thermophysical parameters of interventricular septal myocardium changing with temperature are calculated using Bio-heat Equation based on in vitro experiments, animal experiments, and clinically recorded data, etc., and then the corresponding relation between ablation area and ablation time, ablation energy is also calculated followed by establishment of mathematic function input planning system. Finally, a needle placement proposal is obtained with full coverage of the electrode needles over the target ablation area, in order to guide the surgery.

The next step is to decide on the type of RF electrode needle 108. This depends on the interventricular wall thickness. For example, an RF needle ACT1520 (with an exposure length of 2 cm) would be selected if the wall thickness is ≤25 mm, while an ACT1530 (with an exposure length of 3 cm) would be selected if the wall thickness is greater than 25 mm. These would be single-electrode RF ablation electrode needles that match or correspond to the Medtronic Covidien Cool-tip RF Ablation system, models include ACT1510, ACT1520, and ACT1530, with a total length of 15 cm and a diameter of 17 G. In addition to these needles, RF electrode needles can be provided which take advantage of existing water-cooling circulation functions, and can include new functions such as, but not limited to, ECG monitoring (monitoring of the conduction bundles), frequency conversion (with controllable exposure length), needles that are bendable for required angles along the needle pathway, multi-point ablation (i.e., performing more than one point of ablation along the axial direction of needle), biopsy sampling function, and a drug injection function.

After the above pre-operative steps have been taken, the RF ablation procedure is implemented. With the patient in an operating room, the patient is placed in the supine position under general anesthesia, placing the urinary catheter and conducting internal jugular vein catheterization by percutaneous puncture. As part of this step, a temporary pacemaker can be implanted when necessary (to guard against cardiac arrest), and this can be done by inserting the tubular shell for a temporary pacemaker lead wire.

Next, the ECG monitoring and ultrasound machine 164 is connected to correctly display ECG on ultrasonic screen. This connection can be accomplished by connect the ECG signal output end of the ECG monitor to the ECG signal input end of the ultrasonic instrument using 6.5 mm connectors. The ECG monitor can be from Mindray, and the ultrasound machine can be a Philips color Doppler ultrasonic diagnostic apparatus, model EPIQ 7C. When using the ablation electrode needle system 100 with an ECG monitoring function (i.e., monitoring of the conductive bundles), it is also necessary to connect the ECG monitor to the RF ablation generator 120.

The patient is then connected to the RF ablation apparatus shown in FIG. 1. Specifically, once the RF needle type is confirmed, the package is opened, two negative electrode plates 170 are taken out, and attached to the patient's thighs (avoiding areas with more body hair). Tight attachment is ensured so that there are no air bubbles. One example of an apparatus that can be used is the Medtronic Covidien Cool-tip Radiofrequency Ablation (RFA) system.

The next step is to perform disinfection and drape placement by keeping the patient in the left lateral decubitus position at an angle of about 30°, and then placing a sterile protective sheath for the probe and needle guide. The physician then places a multi-angle trestle and 16G needle guide insert to fix the RF electrode needle. For this step, the following are needed: a sterile protective sheath for the probe, a multi-angle trestle (e.g., made by Phillips), a sterile puncture package (containing needle guide insert), and a sterile coupling agent.

At this point, the ultrasound probe 156 (which can be a S5-1 probe of the Philips EPIQ 7C) is used for preoperative contrast-enhanced ultrasound (CEUS) to locate the myocardial perfusion, and the LOVT PG is recorded. This can be accomplished by using the contrast agent, diluting it in 5 ml normal saline and then shaking it into a homogeneous solution. About 2.0-2.4 ml of the contrast agent can be slowly injected using a syringe over a duration of 30 seconds, followed by a slow injection of 20 ml of normal saline for a duration of 30 seconds. The physician then observes preoperative myocardial perfusion on the ultrasonic screen. The preoperative LVOT PG is observed for comparison with postoperative PG.

The physician then uses the guiding line in apical four or five chamber view to decide the piercing pathway in the apical area. The ultrasound probe 156 (see FIG. 1) is used to decide the piercing pathway in the long or short-axis view in ultrasonic guideline mode. Color Doppler flow imaging (CDFI) is adopted with low rate scale to prevent injuring superficial cardiac blood vessels.

Local anaesthesia is then applied at the intercostal piercing spot through a local subcutaneous injection.

Figure 2A:
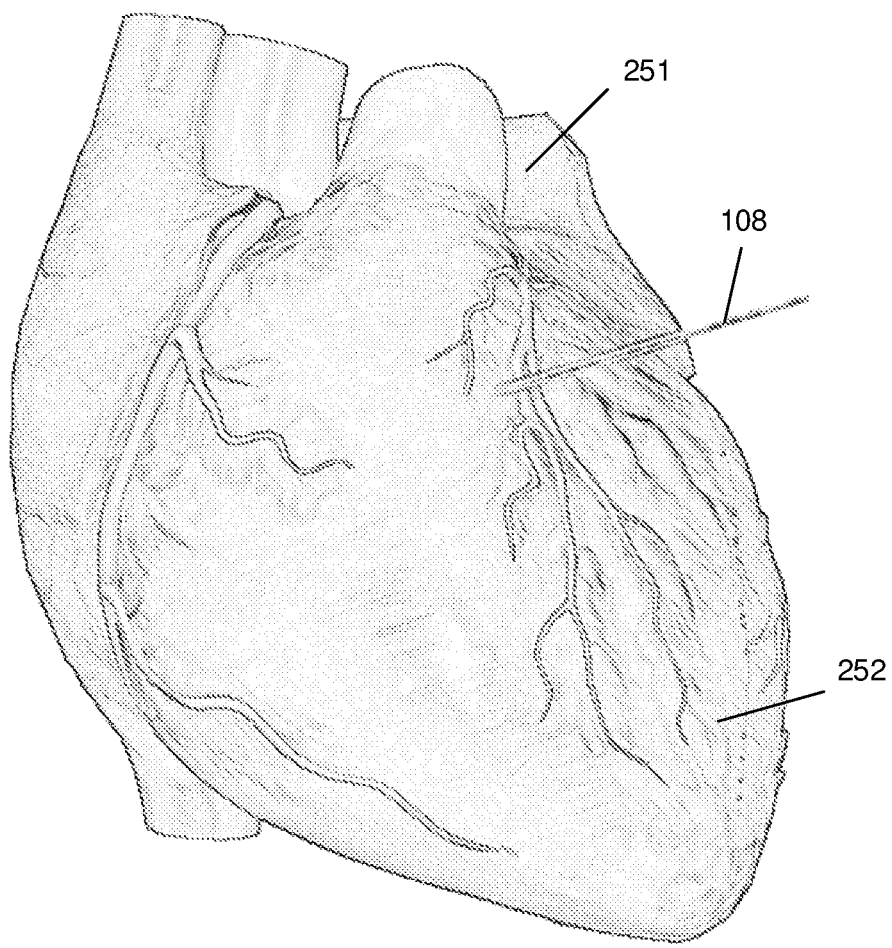
FIG. 2A illustrates a human heart showing the RF electrode needle enters into the interventricular septum along a short axis of the interventricular septum.
Figure 2B:
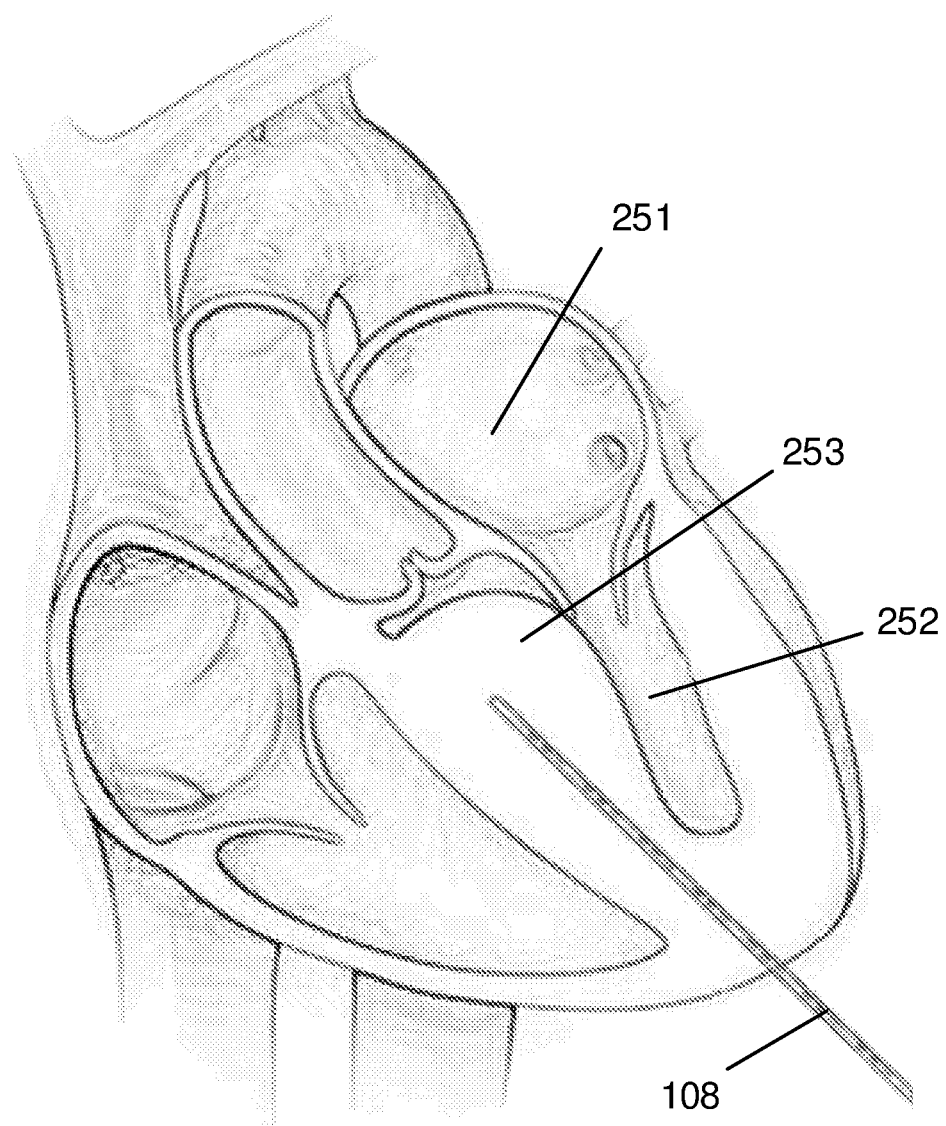
FIG. 2B illustrates a human heart showing the obstruction caused by HCM and the location through which the RF electrode needle of the present invention enters into the interventricular septum according to the present invention.
Figure 2C:
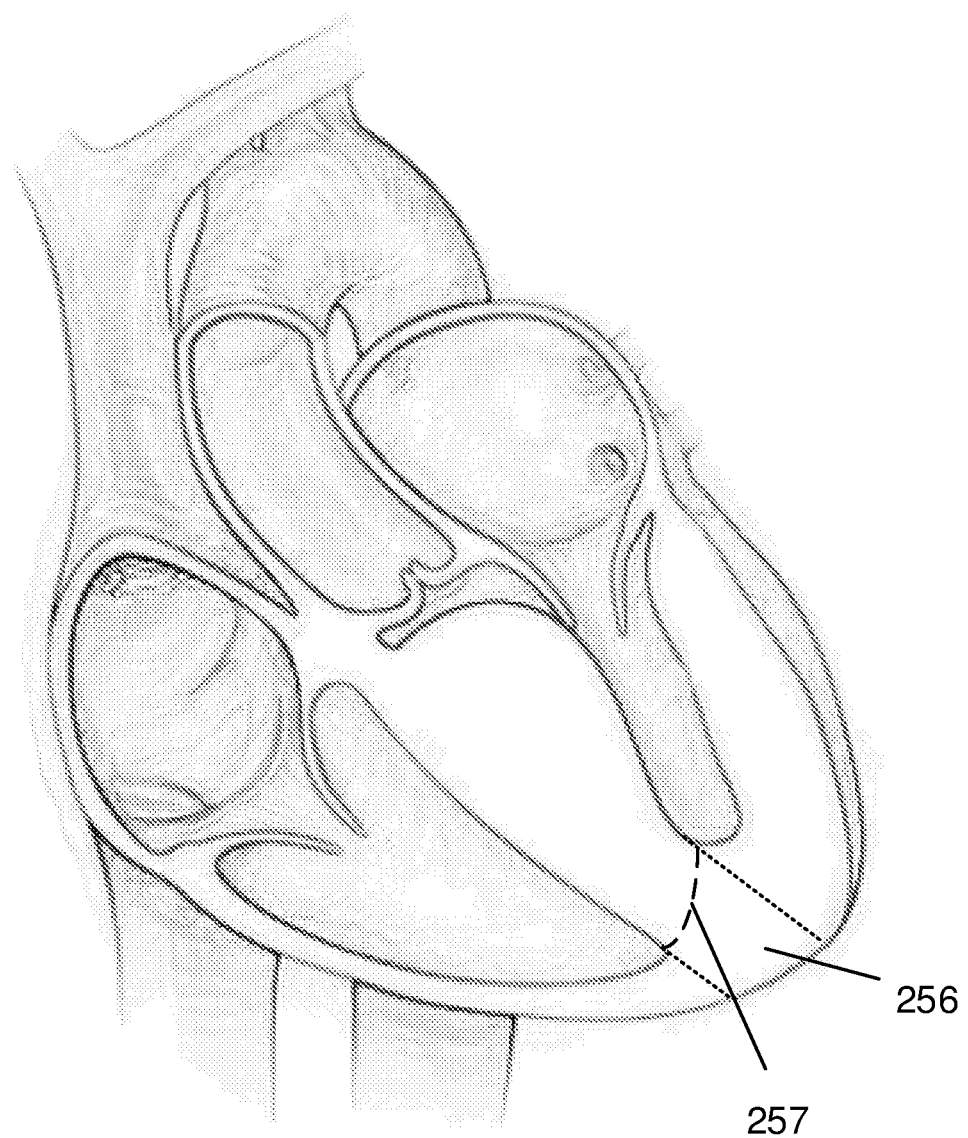
FIG. 2C illustrates a human heart showing the apical area in the direction to which the interventricular septum extends and the connection part of apex and septum.
Figure 3:
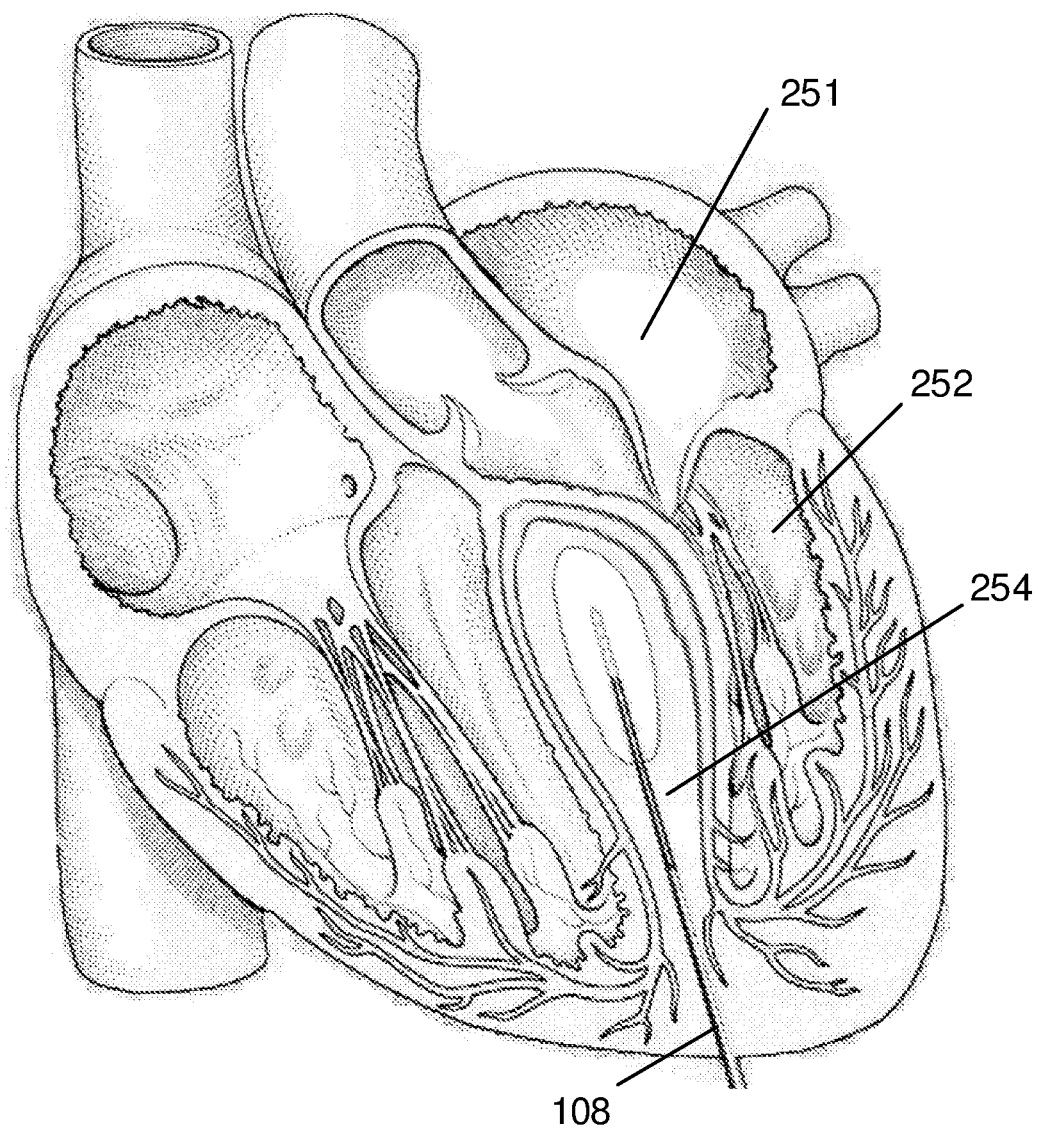
FIG. 3 illustrates a human heart after RF ablation treatment at the posterior interventricular septum according to the present invention.
Figure 4:
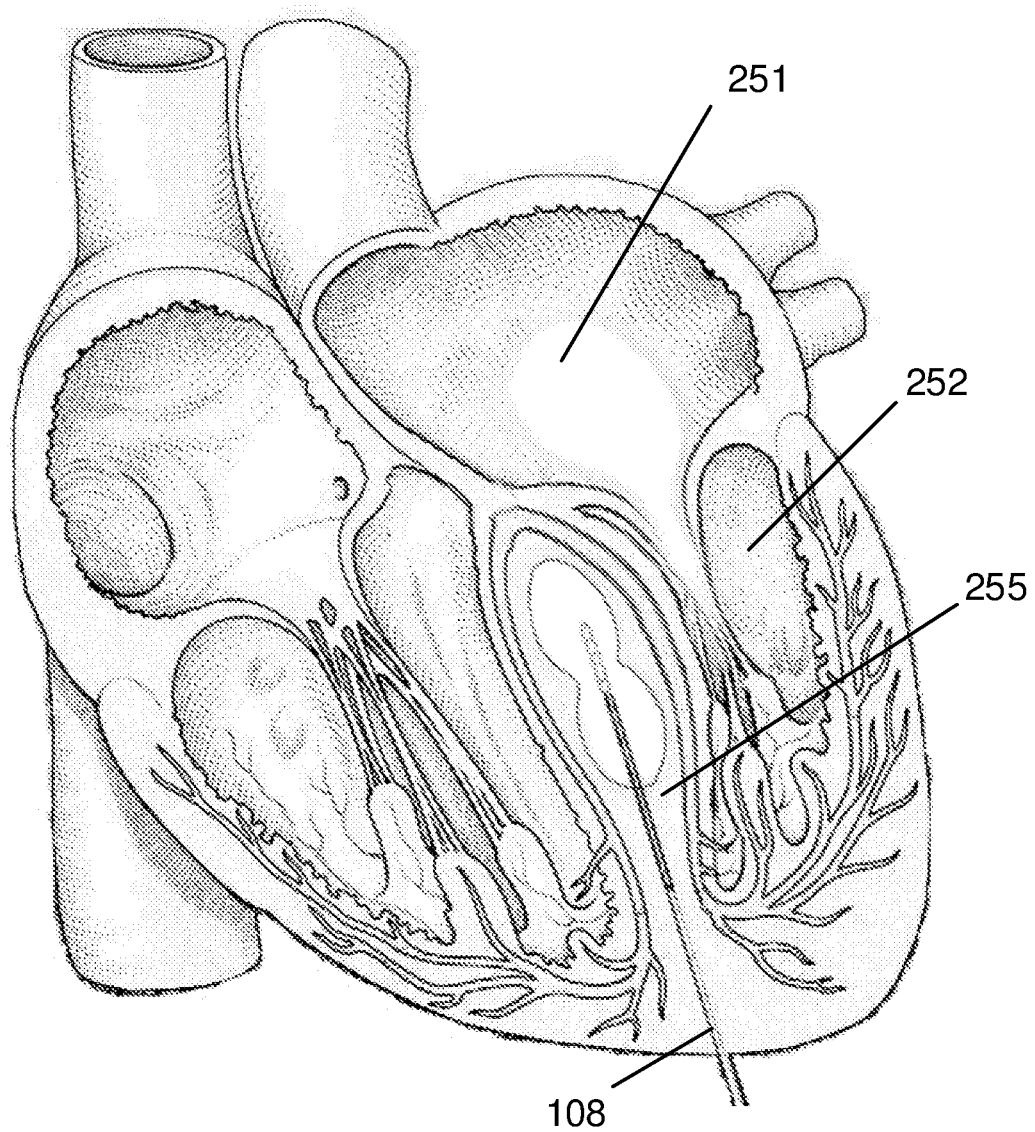
FIG. 4 illustrates a human heart after RF ablation treatment at the anterior interventricular septum according to the present invention.

The RF electrode needle 108 is then introduced to puncture through the epicardium and advance within myocardium, i.e., along an intramyocardial pathway, until reach the hypertrophic area of the ventricular septum. In an embodiment as shown in FIG. 2A, the RF electrode needle 108 reaches the hypertrophic area along a short axis of the ventricular septum, while in the embodiments as shown in FIG. 2B, the RF electrode needle 108 reaches the hypertrophic area along a long axis of the ventricular septum. It is appreciated that, the electrode needle can be introduced to the hypertrophic area via any intramyocardial pathway as long as the electrode is introduced to advance within the myocardium after piercing through the epicardium.

The procedure will be discussed in more detail by taking the preferred example as shown in FIG. 2B. Specifically, the electrode needle 108 is introduced to puncture an apical portion of the interventricular septum 256 to the connection part of apex and septum 257 through the epicardium, and then enters into the interventricular septum 253 and is advanced therein along a middle portion of the interventricular septum 253 between the endocardia at two lateral sides of the interventricular septum 253. The RF electrode needle 108 enters into the interventricular septum 253 through percutaneous intercostal penetration of the patient's chest.

The RF electrode needle 108 is inserted to the hypertrophic area in the basal part of the posterior interventricular septum along the long axis (through the guidance of the ultrasound) of the septum through the parasternal intercostal area, skin, subcutaneous tissue, pericardium, the apical portion of the interventricular septum 256, and the connection part of apex and septum 257 until it reaches a basal part of the interventricular septum 253. This is shown in FIGS. 2B, 2C, 3 and 4. Here, the distance between the basal part of the posterior interventricular septum 255 and a basal portion of the aortic valve is between 2 millimeters to 20 millimeters, and in one embodiment, can be between 5 millimeters to 15 millimeters. During this step, it is important to keep the RF electrode needle 108 in the middle of the interventricular septum 253 to avoid contacting any conduction bundles, and the location of the RF electrode needle 108 will be real-time displayed in the navigational system. The puncture can be accomplished by a semi-automatic puncture process by using robots with four or more-axis mechanical arms. The position of the RF electrode needle 108 and the piercing spot remain relatively static by using ECG gating. The navigational system determines the position of conduction bundle based on, but not limited to, ECG changes during the piercing process. When an ECG change occurs, such as a premature heartbeat, the system will regard it as a warning signal and mark the location of the electrode needle 108 at that moment. The physician uses the navigational system to preset surgical planning and the needle placement proposal to guide the electrode needle 108 to the predetermined position.

Next, the ablation generator 120 is turned on with a power of 60 W. If patient status remains stable for 2 mins, then power is increased to 80 W for 10 minutes. The RF electrode needle 108 is then withdrawn by 1.5 cm along the same pathway at the same power (80 W) for about 12 minutes, and this step can be repeated for any number of times depending on the length of the thickened interventricular septum 253 of the patient. Regarding the existing electrode needles, the ACT1520 has an long axis of 2.6 cm, and a short axis of 2.3 cm, the ACT1530 has an long axis of 3.7 cm, and short axis of 3.1 cm. The number of times the ablation is repeated depends on the size and the thickness of the hypertrophic area of the interventricular septum 253. The RF ablation is maintained for a period of time to achieve the desired treatment effect. See FIG. 3.

In other words, through the repeated withdrawals, the RF electrode needle 108 is withdrawn to the apex without exiting out of the epicardium and reaches an nth position of the hypertrophic area of the ventricular septum along an nth puncture pathway, with n being 1 to 10. In one embodiment of the present invention, n is preferably 2 or 3. In this regard, the interventricular septum 253 along each puncture pathway is provided with N-point ablation, and N is an integer in the range of 1 to 10. In one embodiment of the present invention, N is in the range of 2 to 6. Along each puncture pathway, the centers of each of two adjacent ablation points are spaced from each other by an interval ranging between 5 millimeters and 20 millimeters, and in one embodiment of the present invention, the interval is in the range of 10 millimeters to 15 millimeters.

In addition, the RF ablation generator 120 is turned on to a first power level for a first sub-period of time, and then the power is increased to a second power level which is greater than the first power level for a second sub-period of time, with the ratio of the first power level to the second power level being in the range of 10%-80%. In one embodiment of the present invention, the first power level is 40~60 W and the second power level is 80~120 W.

Next, the pathway is changed to position the electrode needle 108 at a different ablation point, which is the hypertrophic area in the basal part of anterior interventricular septum 254. The ablation generator 120 is turned on and the same steps described above in the previous paragraph are repeated. See FIG. 4, with the arrow illustrating blood flowing from the left atrium 251 to the left ventricle 252. There is an adjusted angle ß between the preceding puncture pathway and the later puncture pathway, and it can be in the range of 5 degrees to 30 degrees. See FIGS. 5A, 5B, 6A and 6B.

During these steps, the filter 200 is used for protection. The filter 200 is delivered by femoral artery puncture or radial artery puncture, and is advanced inversely to the artery. It is used for preventing the patient from cerebral infarction or other tissue infarction caused by embolus such as thrombus and cancer embolus, or dropped tissue fragment, without bringing out any ablated tissue.

Each treatment time for the ablation procedure is in the range of one minute to 30 minutes, and in various embodiments of the present invention, can be in the range of 5 minutes to 15 minutes, or in the range of 8 minutes to 12 minutes.

Figure 5A:
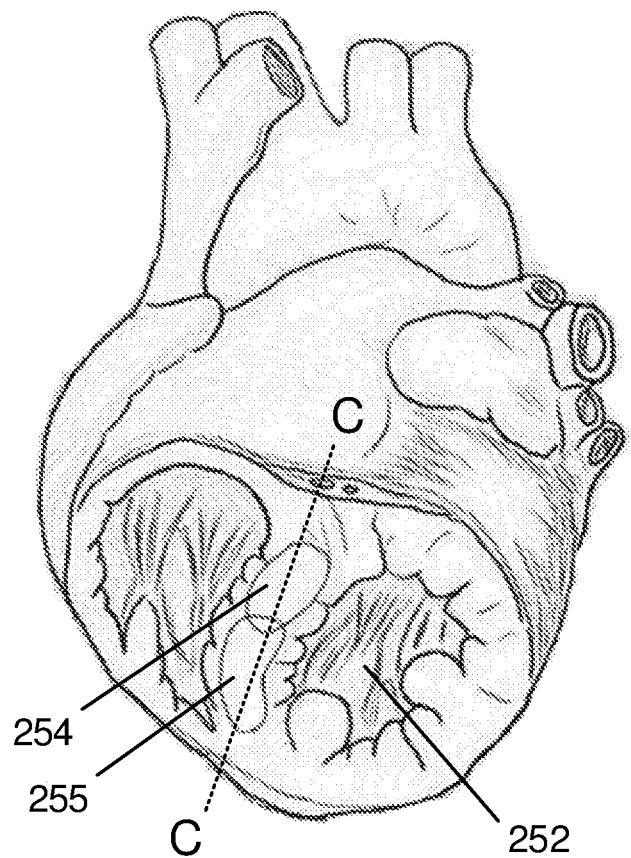
FIG. 5A is a sectional view of a human heart showing the locations of two different puncture pathways.
Figure 5B:
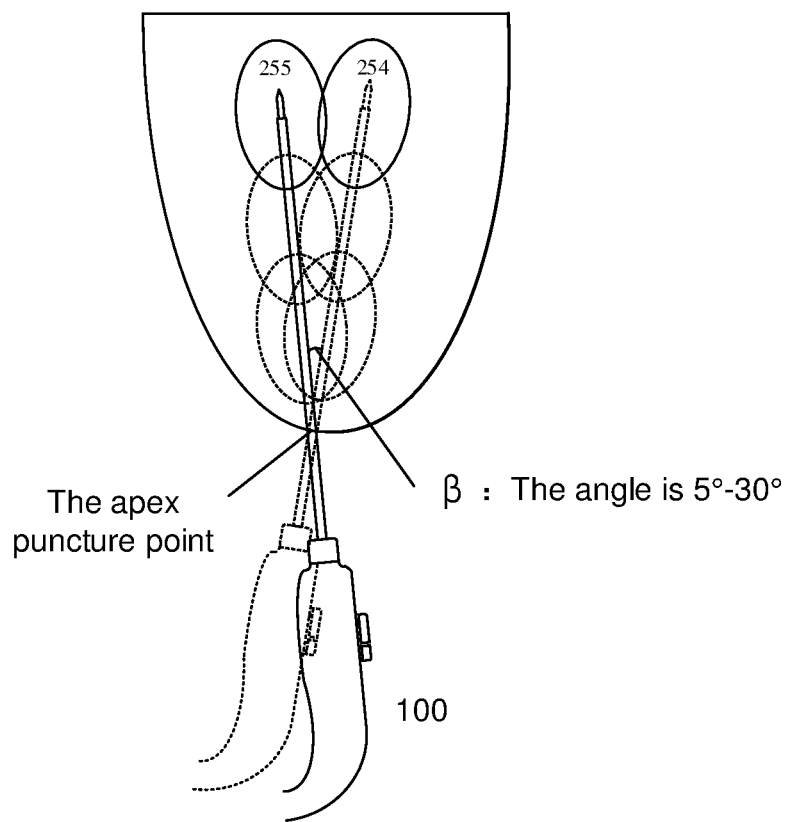
FIG. 5B is a cross-sectional view of the heart of FIG. 5A taken along the line C-C illustrating two different puncture pathways.
Figure 6A:
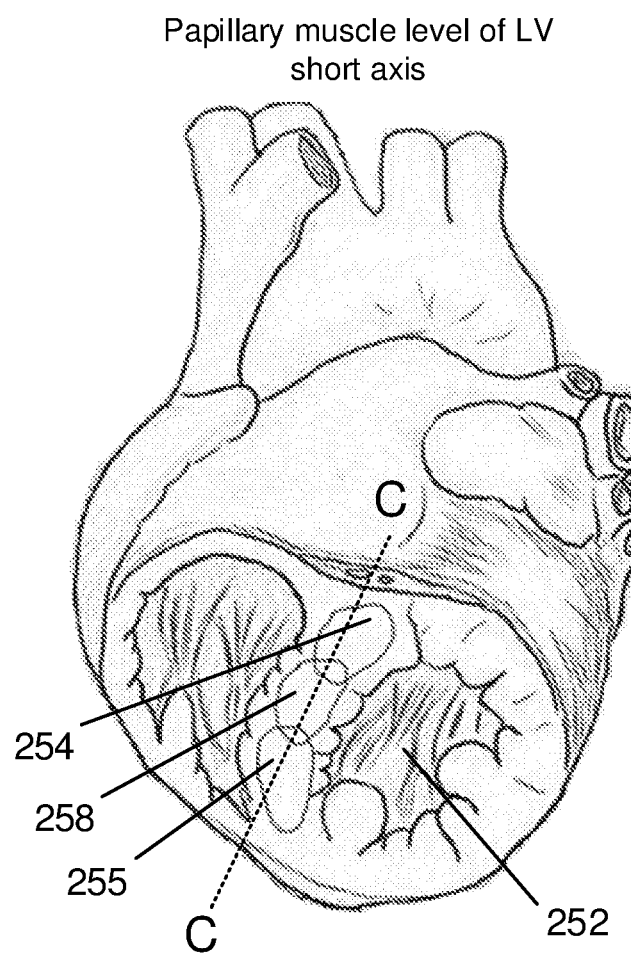
FIG. 6A is a sectional view of a human heart showing the locations of three different puncture pathways.
Figure 6B:
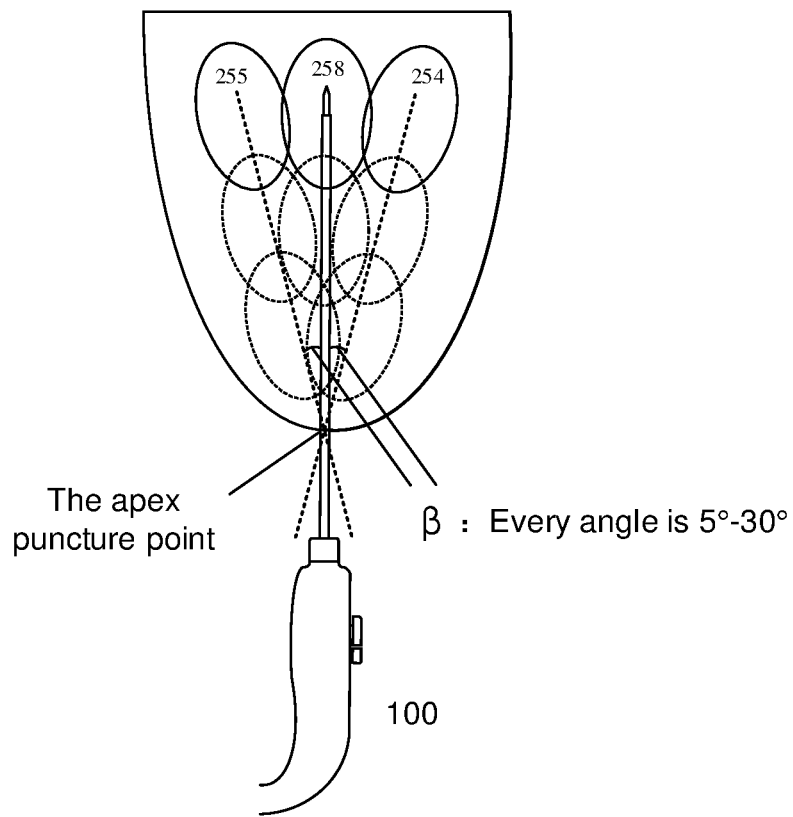
FIG. 6B is a cross-sectional view of the heart of FIG. 6A taken along the line C-C illustrating three different puncture pathways.

Thus, referring to FIGS. 5A and 5B, the posterior interventricular septum 255 is ablated first, and then anterior interventricular septum 254 is ablated. By first performing posterior septal ablation, and then anterior septal ablation, the present invention is able to completely cover the hypertrophic interventricular septal region. In the navigational system, the location of the tip of the electrode needle 108 needs to be real-time displayed so as to allow for the timely adjustment of the electrode needle 108. After one ablation is complete, the system will mark out the ablated area and size in the three-dimensional models to avoid repeated ablation at the same sites. However, in the case where the ventricular septum is very thick, another ablation pathway may be needed, specifically, in the intermediate septum 258 (namely, the part between the posterior interventricular septum 255 and the anterior interventricular septum 254). As shown in FIGS. 6A and 6B, the posterior interventricular septum 255 is first ablated, then the anterior interventricular septum 254 is ablated, and then the intermediate septum 258 is ablated, thereby achieving an overall ablation effect by points into a line, lines into a side and sides into a volume. However, as the puncture point remains unchanged at the apical portion, changing from one pathway to another pathway requires simply changing the orientating direction of the electrode needle 108 without the need for another puncture location, as best shown in FIGS. 5A, 5B, 6A and 6B. The area to be ablated can be determined according to the hypertrophic area which is clarified by a plurality of imaging examinations (such as ultrasound, CT, magnetic resonance) before the treatment, with safety boundaries of the conduction bundle reserved. The type of the electrode needle 108 is determined according to the area to be ablated in consideration of ablation sizes and ranges by each ablation of different types of electrode needles, and thus deciding the ablation planning, including i.e. determining how many pathways, and how many ablation points for each pathway, etc. to perform the treatment.

Some examples of treatment are illustrated in the following table.

TABLE 1

| Thickness of the hypertrophic interventricular septum | Type and parameter of the electrode needle | Power of the electrode needle | Ablation pathway | Number of ablation points and power level |
| --- | --- | --- | --- | --- |
| 15-20 mm | ACT1510 Length of the needle: 15 cm; Diameter: 17 G; Exposure length at the tip: 10 mm. | 40-60 W | posterior interventricular septum; anterior interventricular septum. | Each pathway has 2-3 ablation points 1) initiates with a power of 40 W, if the patient status remains stable for 2 mins, then power is increased to 60 W, with a total period of time 12 mins. 2) The electrode needle is withdrawn by 1.5 cm along the same pathway with the same power of 60 W, 12 mins. 3) The electrode needle is withdrawn again by 1.5 cm along the same pathway with the same power of 60 W, 12 mins. |
| 21-30 mm | ACT1520 Length of the needle: 15 cm; Diameter: 17 G; Exposure length at the tip: 20 mm. | 60-80 W | posterior interventricular septum; anterior interventricular septum. | Each pathway has no less than 3 ablation points. 1) initiates with a power of 60 W, if the patient status remains stable for 2 mins, then power is increased to 80 W, with a total period of time 12 mins. 2) The electrode needle is withdrawn by 1.5 cm along the same pathway with the same power of 80 W, 12 mins. 3) The electrode needle is withdrawn again by 1.5 cm along the same pathway with the same power of 80 W, 12 mins |
| 31 mm or above | ACT1510 Length of the needle: 15 cm; Diameter: 17 G; Exposure length at the tip: 20 mm. | 80-100 W | posterior interventricular septum; anterior interventricular septum; intermediate spetum. | Each pathway has no less than 3 ablation points. 1) initiates with a power of 80 W, if the patient status remains stable for 2 mins, then power is increased to 100 W, with a total period of time 12 mins. 2) The electrode needle is withdrawn by 1.5 cm along the same pathway with the same power of 100 W, 12 mins. 3) The electrode needle is withdrawn again by 1.5 cm along the same pathway with the same power of 100 W, 12 mins. |

The system of FIG. 1 can also provide several important features to enhance the effectiveness of the procedure. For example, based on the existing water-cooling circulation function provided by the ice water box 166 and the pump 152, the following functions can be added, including: (i) frequency conversion (with controllable exposure length), which can be used to control the area size of the single-point ablation; (ii) the electrode needle 108 can be made bendable for certain required angles, which can lower the level of difficulty in dealing with angular changes of the electrode needle; (iii) multi-point ablation (i.e., simultaneously performing more than one point of ablation along the axial direction of needle); (iv) segmented ablation based on parameter setting in order to reduce the number of times the needle 108 is withdrawn, and to shorten the surgery time; (v) biopsy sampling; and (vi) drug injection.

Throughout the entire procedure, the ultrasound machine 164 is operated and adjusted to document images and to evaluate LVOT PG. The ablation position, time, and power are recorded. In addition, the patient's ECG, blood pressure, and blood oxygen saturation are monitored through the whole procedure. In this regard, the ECG monitoring system, which includes the RF electrode needle 108 (which has an ECG detection function) and ECG monitoring equipment, can monitor real-time heart rate, blood pressure, blood oxygen, respiratory rate and other vital signs. It can also record intraoperative arrhythmia.

Next, the RF electrode needle 108 is withdrawn, and pressure is applied to the pierce (puncture) point for 3-5 mins. CEUS is then performed to show the contrast agent filling defect in the interventricular septum. Due to the small diameter of the RF electrode needle 108 and the small pinhole, the procedure causes almost no hemorrhage.

Thus, according to the method of the present invention, the RF electrode needle 108 is inserted directly through the interventricular septum where there are minimal conduction bundles.

The Electrode Needle

Figure 7:
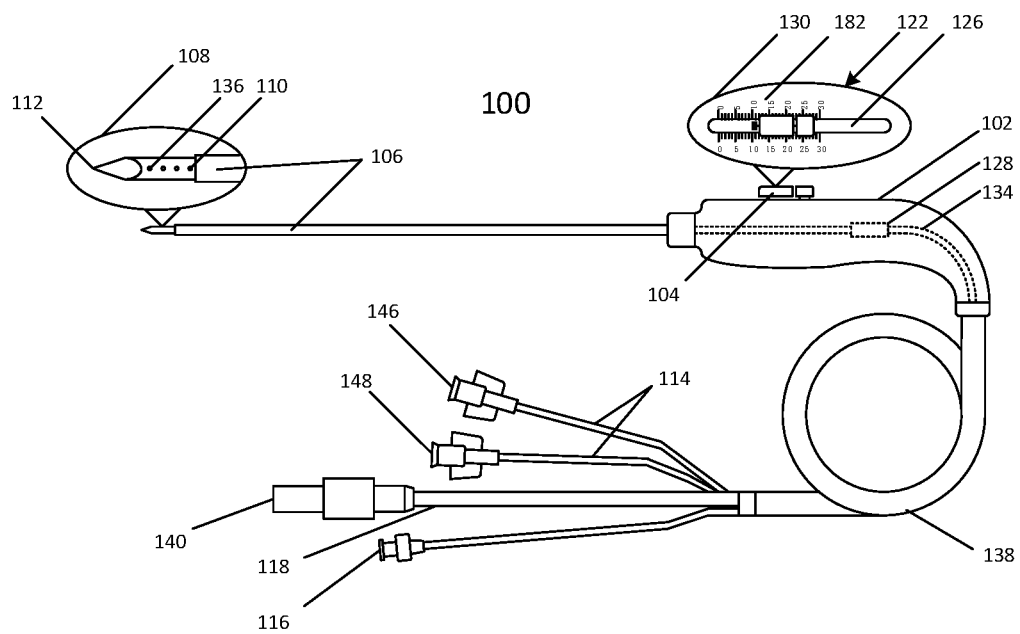
FIG. 7 is an overall structural view of a multifunctional radio frequency ablation electrode needle system.
Figure 8A:
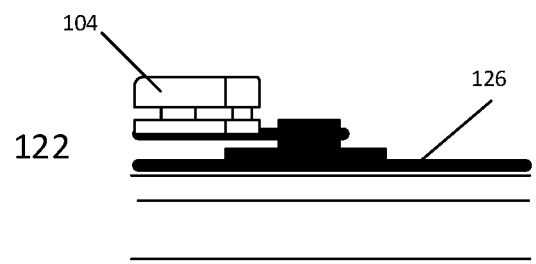
FIG. 8A is a cross-sectional side view of the needle tubing of the electrode needle system of FIG. 7 illustrating the connection between the button and the track structure for the handle of the needle system.
Figure 8B:
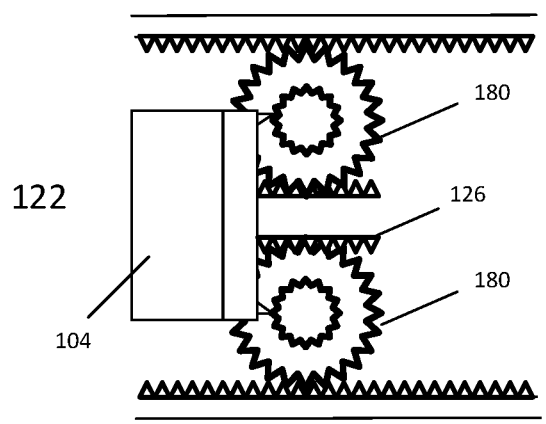
FIG. 8B is a top cross-sectional view of the needle tubing of the electrode needle system of FIG. 7.
Figure 9:
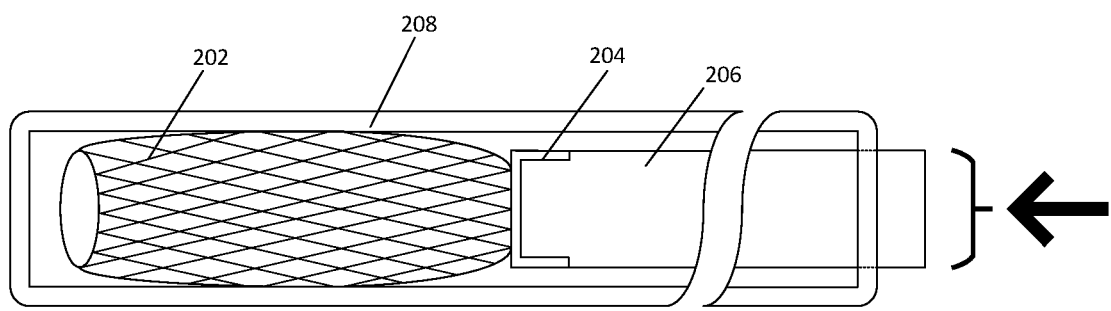
FIG. 9 is a side view of a retrievable vascular filter placement assembly according to the present invention shown compressed inside an arterial sheath.

Referring to FIGS. 7, 8A and 8B, the present invention provides a multifunctional radio frequency ablation electrode needle system 100. The electrode needle system 100 includes a handle 102 having an adjustment button 104 and a needle tubing 106 for adjusting the length of exposure for the electrode, an electrode needle 108 having a plurality of infusion holes 110 adjacent its tip 112, a circulating water cooling pipe 114, an infusion tube 116, and a radio frequency power line 118. The infusion tube 116 can be directly connected to various injection syringes. The infusion tube 116 can be a conventional transparent infusion tube connector with an injector that is provided with a universal check valve (not shown) for connection with various injection syringes. The radio frequency power line 118 is wrapped in an electric cable and is connected to the radio frequency generator 120 (see FIG. 1).

The handle 102 is provided therein with a track system 122 extending along the needle tubing 106. The track system 122 is provided thereon with the button 104 that is connected to a track 126 (which has teeth) by gears 180 (see FIGS. 8A and 8B) and movable along the track 126. The needle tubing 106 is fixed relative to the button 104. As the button 104 is moved along the track 126 under the action of the gears 180, the button 104 drives the needle tubing 106 to a corresponding movement, so as to change the length that the electrode needle 108 is exposed.

The RF electrode needle 108 has a temperature measuring point 136 which is connected to a thermocouple 128. The thermocouple 128 is located inside the handle 102. One end of the thermocouple 128 is connected with a thermocouple compensating line 134 which extends into the electric cable 138. The thermocouple 128 functions to measure in real time the treatment temperature of the ablated pathological tissue. The thermocouple 128 may be an alloy of copper and nickel used especially for electrical resistors and in conventional thermocouples. The thermocouple compensating line 134 and the radio frequency power line 118 are jointly disposed inside the electric cable 138. A proximal end of the radio frequency power line 118 is connected with a quick-release electrical connector 140.

A transparent observation window 130 and a scale 182 are disposed outside the button 104. The position indication line of the button 104 is aligned with the scale 182 of the handle 102.

The circulating water cooling pipe 114 is a water pipe having a blue water inlet end 146 and a transparent water outlet end 148, and provided with a quick-release pipe one-way coupling (not shown), including a Ruhr check value female connector and a Ruhr check value male connector.

During use, a doctor can hold the handle 102 with a single hand, move the button 104 with his/her thumb to slide back and forth along the track 126 and drive the needle tubing 106 to move. The track 126 can be in contact with the bottom of the button 104, and is provided with a gear structure. The position indication line of the button 104 is aligned with a scale 182 of the handle 102. Whether the button 102 has begun sliding, that is, whether the gears 180 have begun rotating, can be determined according to the sound of gear engagement.

During actual treatment, the radio frequency power line 118 is connected to a corresponding interface of the radio frequency generator 120. The water inlet end 146 and the water outlet end 148 of the circulating water cooling pipe 114 are each connected to an extension water pipe (not shown) of the corresponding color by means of a Ruhr check valve (not shown). The infusion tube 116 may be connected to an infusion apparatus directly or by means of an extension pipe (not shown). Before use, air can be squirted out by pre-filling a drug or saline. After the connection of the electrode needle is completed, the extension pipe of the water inlet end 146 is disposed in the circulating pump 152 (see FIG. 1). The pump 152 is turned on to expel the air inside the circulating water cooling pipe 114.

During the procedure, under imaging (ultrasound, CT, or MR) guidance through the ultrasound probe 156, after the puncture point is accurately determined, the electrode needle 108 is inserted. After the electrode needle 108 reaches the pre-ablation site, the radio frequency generator 120 is adjusted, and treatment parameters are set, to start the treatment. During the treatment, the thermocouple 128 measures in real time the treatment temperature of the ablated pathological tissue, to prevent carbonization on the exposed surface of the tip of the electrode 108, thereby protecting the ablated tissue. During radio frequency ablation, liquids such as saline, alcohol, and a chemotherapy solution can be injected into the pathological tissue by means of the infusion tube 116 at the same time, so that the range of ablation can further be enlarged.

Because the needle tubing 106 is connected to the button 104 inside the handle 102, when the button 104 moves back and forth along the track 126 inside the handle 102, the button 104 drives, by means of the gears 180, the needle tubing 106 to move, so as to change the exposure length of the electrode needle, thereby adjusting the range of ablation. Thus, the needle system 100 of the present invention can be applied to complex multi-ablation environments having high requirements on the range of ablation. The present invention provides large span and high precision with the use of the gear structure for button control, can achieve precise ablation treatment, and has high clinical applicability.

Arterial Filter

The present invention provides a retrievable vascular filter placement assembly 200 that is applicable during the radio frequency ablation, or a period of time after the radio frequency ablation, and which is adapted to be placed in an aorta to filter thrombus, embolus or other tissue debris in a screen form without diminishing the blood flow in the aorta, so as to prevent embolic complications. The filter assembly according to the present invention can prevent complications such as embolism, can significantly reduce the intraoperative and postoperative embolism risks, increase the safety of the procedure, and improve the prognosis for patients.

Referring to FIGS. 9-16, the retrievable vascular filter placement assembly 200 includes a filter 210. The filter 210 includes a main screen 202 that is braided by medical nickel-titanium shape memory alloy wires, a main-screen connecting member 204 that can be made of ultra-smooth coated stainless steel, and a main-screen placement guide wire 206. The guide wire 206 can be made of ultra-smooth coated stainless steel having a diameter of 4-5 mm, and preferably, 0.4826 mm, (i.e., 0.19 inch). The placement process requires the use of an 18F arterial sheath 208.

The arterial sheath 208 is first introduced into the femoral artery or the radial artery via conventional percutaneous puncture. Specifically, the arterial sheath 208 is the sheath tube of the filter 210 and is delivered to the location between the arcus aortae and the aortic valve by means of a femoral artery puncture via the thigh, or a radial artery puncture via the wrist, in a vascular intervention manner, which is a different pathway from the puncture pathway via which the electrode needle 102 enters into the interventricular septum from the apex. The sheath 208 is continuously adjusted and moved to the ascending aorta. Then the filter 210 is introduced via the sheath 208, and the main screen 202 is compressed to the state shown in FIG. 9. When the filter 210 is at the desired location, the guide wire 206 is pushed out (see arrow A1) so as to release the filter 210 from the sheath 208, and the main screen 202 unfolds automatically due to its shape memory characteristic.

Figure 10:
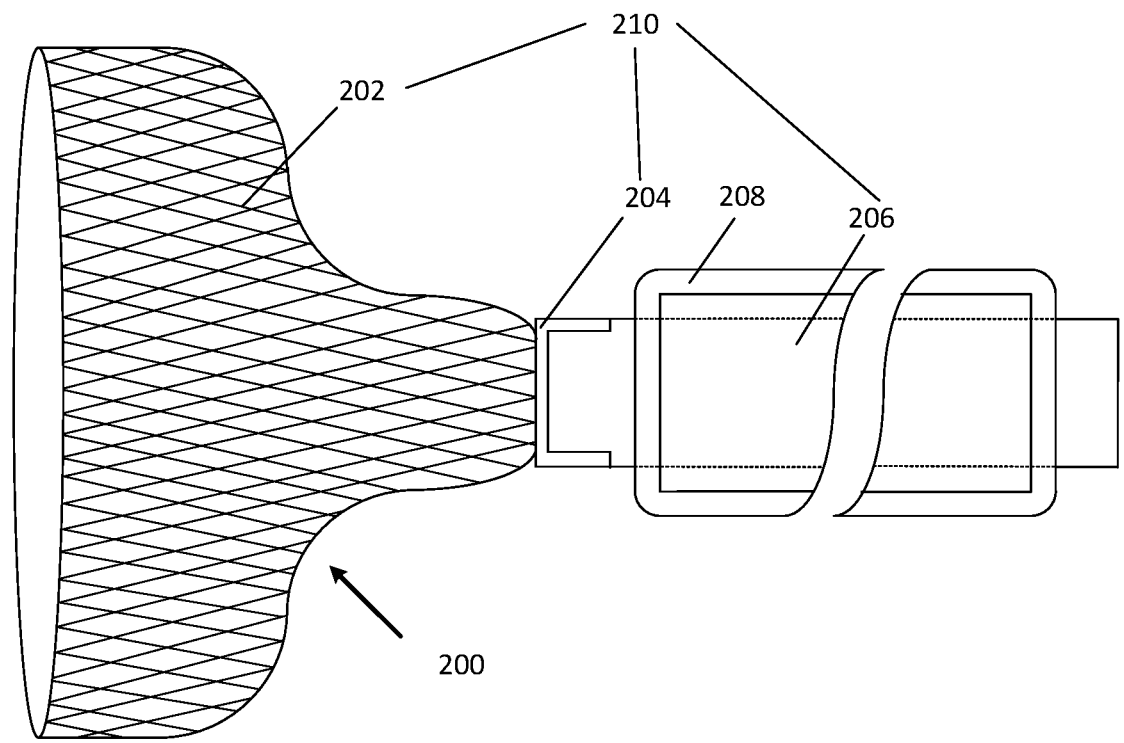
FIG. 10 is a side view of the retrievable vascular filter placement assembly of FIG. 9 shown with the main screen opened.

After the filter 210 is released, the main screen 202 unfolds automatically and the state shown in FIG. 10 is reached. The length of the main screen 202 is 2-4 cm, preferably, 3 cm. The maximum diameter of the main screen 202 is determined by the diameter of the aorta. The pocket structure of the main screen 202 has a length of 1 m and a diameter of 1 cm. The placement of the main screen 202 is completed after the main screen 202 is fixed to the arterial wall.

Figure 11:
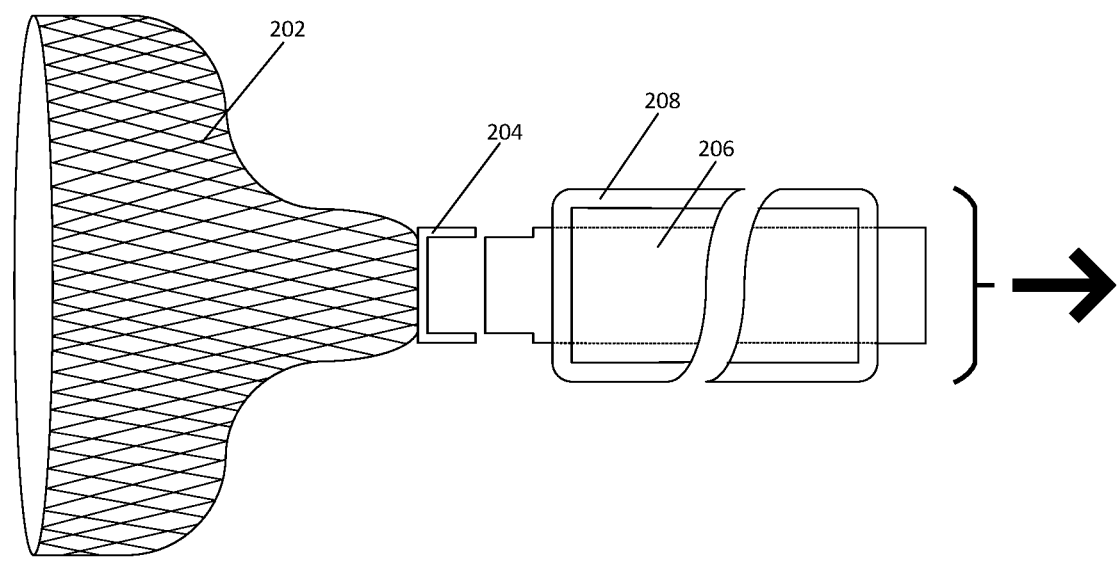
FIG. 11 is a side view of the retrievable vascular filter placement assembly of FIG. 9 shown with the sheath and guide wire separated from the main screen.
Figure 12:
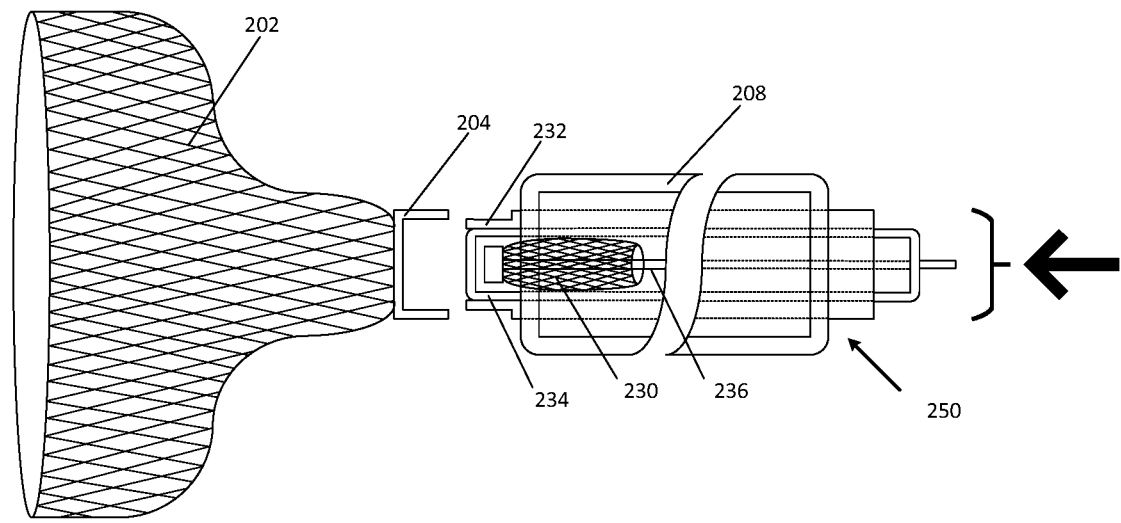
FIG. 12 is a side view of a vascular filter retrieving assembly according to the present invention shown compressed inside an arterial sheath and delivered to the location of the main screen.

After the placement of the main screen 202 is completed, the guide wire 206 is rotated anticlockwise, so as to release the threaded connection between the guide wire 206 and the connecting member 204, as shown in FIG. 11. The sheath 208 and the guide wire 206 are taken out at the same time.

Referring to FIGS. 12-16, a retrievable artery filter retrieving assembly 250 according to the present invention includes a secondary screen 230 that is braided by medical nickel-titanium shape memory alloy wires, a secondary-screen connecting member 232 that can be made of ultra-smooth coated stainless steel, a 9F secondary screen sheath 234, and a secondary-screen placement guide wire 236. The guide wire 236 can be made of ultra-smooth coated stainless steel, having a diameter of 0.5-1 mm, preferably, 0.9652 mm, i.e., 0.038 inch. The retrieving process requires the use of an 18F arterial sheath 208.

The arterial sheath 208 is introduced into the femoral or radial artery by percutaneous puncture. The sheath 208 is continuously adjusted and moved to the main screen 202 that is near the ascending aorta. Then, the retrievable artery filter retrieving assembly 250 is introduced via the sheath 208 to the position shown in FIGS. 12 and 13. Further, as indicated by the arrow A3, the secondary-screen connecting member 232, the secondary screen sheath 234, and the secondary-screen placement guide wire 236 are pushed out at the same time.

Figure 13:
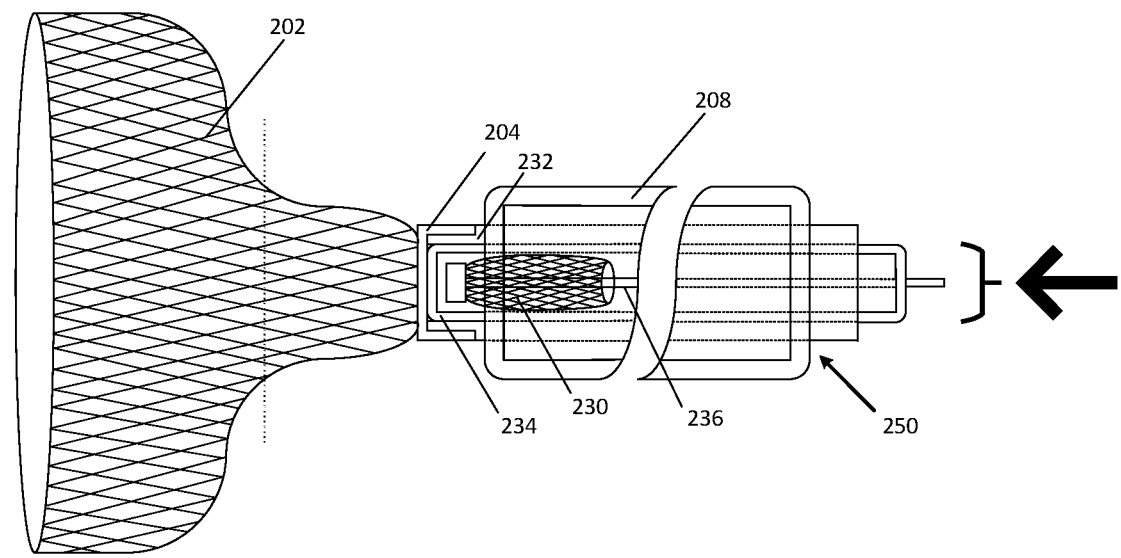
FIG. 13 is a side view of the vascular filter retrieving assembly of FIG. 12 shown with its secondary screen connecting member coupled to the main screen connecting member.

The secondary-screen connecting member 232 has a magnetic structure that can be automatically butt-connect to the main-screen connecting member 204. After the butt-connection, the secondary-screen connecting member 232 is rotated clockwise, so that the secondary-screen connecting member 232 is threadedly connected to the main-screen connecting member 204, as shown in FIG. 13.

Figure 14:
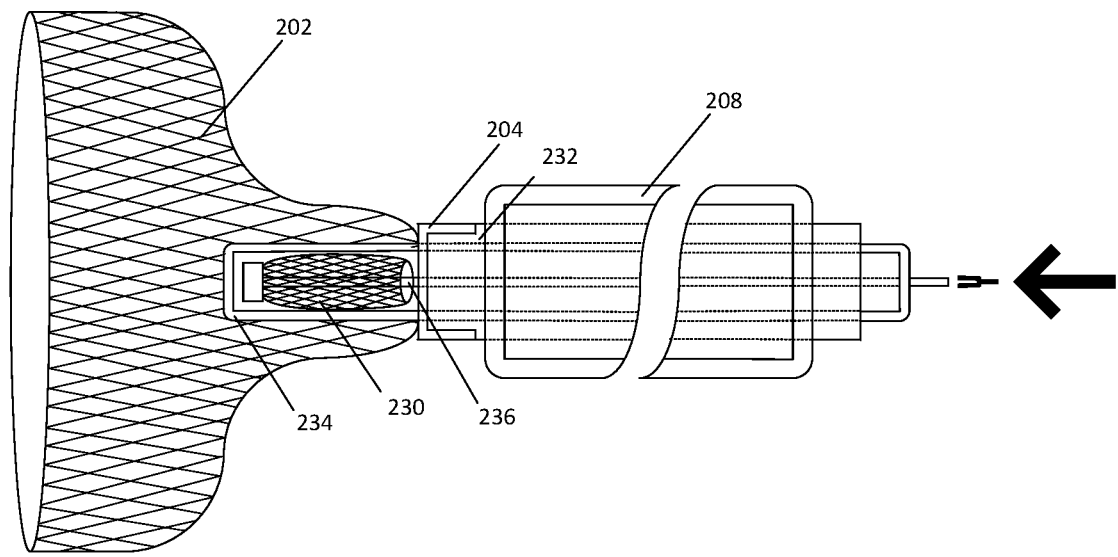
FIG. 14 is a side view of the vascular filter retrieving assembly of FIG. 12 shown with the secondary screen sheath and the secondary-screen placement guide wire pushed out distally to break through the mesh structure in the middle of the main-screen connecting member.
Figure 15:
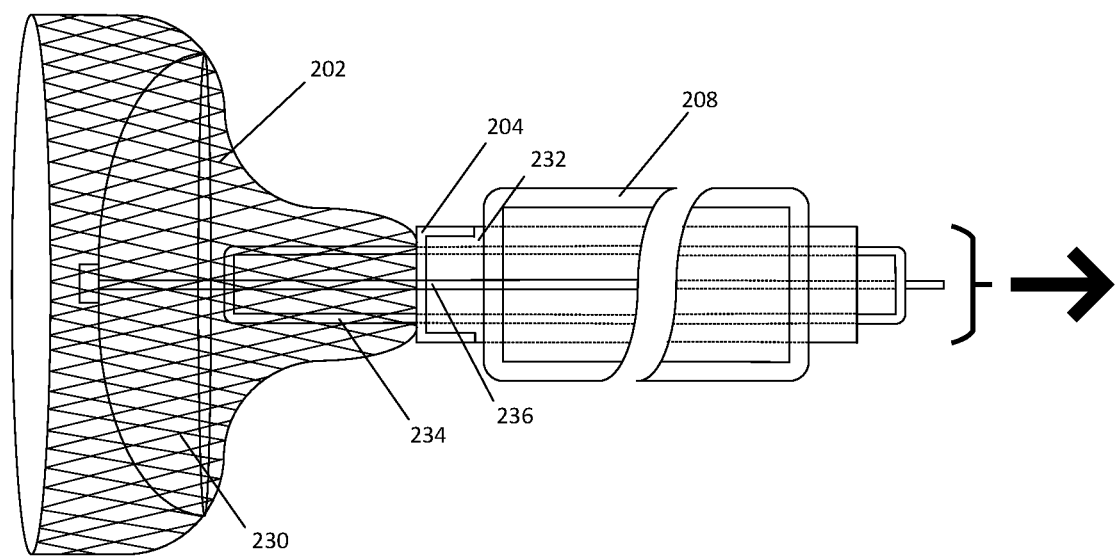
FIG. 15 is a side view of the vascular filter retrieving assembly of FIG. 12 shown with the secondary screen unfolded.
Figure 16:
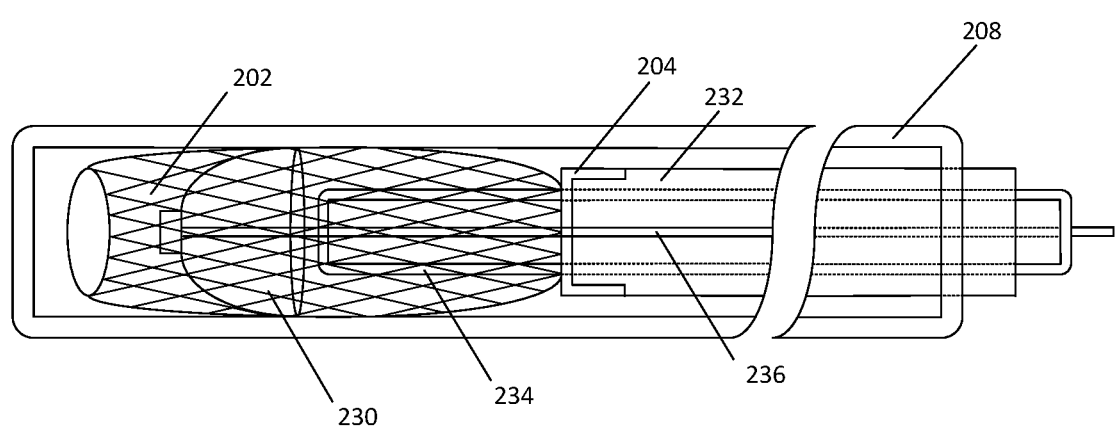
FIG. 16 is a side view of the vascular filter retrieving assembly of FIG. 12 shown with the entire artery filter pulled back into the arterial sheath.

After being pushed out at the same time, the secondary screen sheath 234 and the secondary-screen placement guide wire 236 can break through the mesh structure in the middle of the main-screen connecting member 204, to expose the front end of the secondary screen sheath 234, as shown in FIG. 14. The secondary screen sheath 234 extends beyond the main-screen connecting member 204 by at least 1 cm, thereby effectively preventing the falling of thrombus, embolus or other tissue debris when the secondary screen unfolds. Further, as indicated by the arrow A6 in FIG. 14, the secondary-screen placement guide wire 236 is pushed out, so that the secondary screen 230 unfolds automatically. See FIG. 15. The length of the secondary screen 230 can be about 1 cm. The maximum diameter of the secondary screen 230 is determined by the diameter of the main screen 202. As shown in FIG. 15, by pushing out the secondary-screen connecting member 232, the secondary screen sheath 234, and the secondary-screen placement guide wire 236, the entire structure (except the arterial sheath 208) can be retrieved.

When the entire artery filter 200 is pulled back into the arterial sheath 208 (see FIG. 16), thrombus, embolus or other tissue debris is captured between the main screen 202 and the secondary screen 230 and can therefore be removed. Then, the entire arterial sheath 208 is removed, thereby completing the retrieval of the artery filter 200.

The filter 200 can be positioned in the aorta by being inversely advanced in the artery. It is used for preventing the patient from experiencing cerebral infarction or other tissue infarction caused by embolus such as thrombus and cancer embolus, or dropped tissue fragment.

The above detailed description is for the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, components, mechanisms and methods are omitted so as to not obscure the description of the present invention with unnecessary detail.

The invention claimed is:

1. A method for treating hypertrophic cardiomyopathy (HCM), comprising the steps of:
   providing an RF ablation electrode needle system comprising an RF ablation generator, and an electrode needle;
   introducing the electrode needle to puncture within myocardium and to reach a hypertrophic area of an interventricular septum;
   turning on the RF ablation generator to implement single-point or multi-point ablation on the hypertrophic area of the interventricular septum; and
   withdrawing the electrode needle from a patient;

wherein the electrode needle reaches the interventricular septum via an apical portion of the interventricular septum, through the connection part of an apex and the septum.

2. The method of claim 1, wherein the electrode needle is introduced to puncture a connection part of an apex and the septum, and then enter into the interventricular septum and be advanced therein along a middle portion of the interventricular septum between the endocardia at two lateral sides of the interventricular septum.

3. A method for treating hypertrophic cardiomyopathy (HCM), comprising the steps of:
providing an RF ablation electrode needle system comprising an RF ablation generator, and an electrode needle;
introducing the electrode needle to puncture within myocardium and to reach a hypertrophic area of an interventricular septum;
turning on the RF ablation generator to implement single-point or multi-point ablation on the hypertrophic area of the interventricular septum; and
withdrawing the electrode needle from a patient;
wherein the electrode needle enters into an apical portion of the interventricular septum through an epicardium.

4. The method of claim 3, further comprising a step of using an imaging equipment for displaying the myocardium.

5. The method of claim 4, wherein the imaging equipment is an ultrasound monitoring device or Magnetic Resonance Imaging device.

6. The method of claim 3, wherein the electrode needle is prevented from contacting conduction bundles at an endocardia during the puncture process.

7. The method of claim 3, further comprising an ECG monitoring equipment to monitoring ECG data throughout an entire procedure in real time so as to allow for adjustment of the electrode needle when a change of the ECG data is detected.

8. The method of claim 3, wherein the electrode needle reaches a basal part of the interventricular septum which is defined as a first ablation site, and a puncture pathway to reach the first ablation site is a first puncture pathway.

9. The method of claim 8, wherein a basal part of the interventricular septum is a basal part of an anterior interventricular septum, a basal part of a posterior interventricular septum, or a basal part of an intermediate septum between the anterior interventricular septum and the posterior interventricular septum.

10. The method of claim 8, wherein the first ablation site is spaced from a basal portion of the aortic valve by a distance between 2 millimeters to 20 millimeters.

11. The method of claim 8, wherein the RF ablation generator is turned on to apply RF energy at the first ablation site for a first predetermined period of time.

12. The method of claim 11, wherein after ablation at the first ablation site, the electrode needle is withdrawn by a predetermined distance to a second ablation site for ablation for a second predetermined period of time, the second predetermined period of time being equal to or not equal to the first predetermined period of time.

13. The method of claim 12, wherein after ablation at the second ablation site, the electrode needle is withdrawn by a third predetermined distance to a third ablation site for ablation for a third predetermined period of time, the third predetermined period of time being equal to or not equal to the first predetermined period of time and/or the second predetermined period of time.

14. The method of claim 13, wherein after ablation at a previous ablation site, the electrode needle is withdrawn by a predetermined distance to an Nth ablation site for ablation for a predetermined period of time, and wherein N is greater than 3.

15. The method of claim 3, wherein the RF ablation generator supplies a power level ranging between 30W and 150W for each of the single-point or multi-point ablations.

16. The method of claim 3, wherein the electrode needle reaches an nth position of the hypertrophic area of the interventricular septum along an nth puncture pathway, and wherein n is 1, 2, 3 or 4.

17. The method of claim 16, wherein the interventricular septum along each puncture pathway is applied with N-point ablation, and N is an integer in the range of 1 to 10.

18. The method of claim 16, wherein along each puncture pathway, centers of each of two adjacent ablation points are spaced from each other by an interval ranging between 5 millimeters and 20 millimeters.

19. The method of claim 11, wherein when ablation is conducted at the first ablation site, the RF ablation generator is turned on to a first power level for a first sub-period of time, and then the power is increased to a second power level which is greater than the first power level for a second sub-period of time.

20. The method of claim 19, wherein the ratio of the first power level to the second power level is in the range of 10%-80%.

21. The method of claim 20, wherein the first power level is 40-60W and the second power level is 80-120W.

22. The method of claim 3, wherein a total treatment time for an ablation procedure is in the range of one minute to 30 minutes.

23. The method of claim 16, wherein n is greater than 2, and wherein the electrode needle is introduced into another position of the hypertrophic area of the interventricular septum along a later puncture pathway after ablation has been performed on a preceding puncture pathway without the electrode needle being withdrawn out of an epicardium of an apex.

24. The method of claim 23, wherein an adjusted angle between the preceding puncture pathway and the later puncture pathway is in a range of 5 degrees to 30 degrees.

25. The method of claim 3, wherein the electrode needle reaches the hypertrophic area of the interventricular septum along a long axis which is parallel to an extension direction of the interventricular septum from the apical portion to a basal part adjacent to left and right artriums.

26. The method of claim 3, wherein the interventricular septum comprises a posterior interventricular septum and an anterior interventricular septum arranged in sequence along a short axis which is perpendicular to an extension direction of the interventricular septum from the apical portion to a basal part adjacent to left and right atriums; wherein the posterior interventricular septum is ablated first, and then the anterior interventricular septum is ablated.

27. The method of claim 3, wherein the electrode needle is prevented from piercing through an ventricle during a puncture process.

28. The method of claim 3, wherein the electrode needle is prevented from piercing through an endocardia during a puncture process.

29. A method for treating hypertrophic cardiomyopathy (HCM), comprising the steps of:
providing an RF ablation electrode needle system comprising an RF ablation generator, and an electrode needle;

introducing the electrode needle to puncture within myocardium and to reach a hypertrophic area of an interventricular septum;
turning on the RF ablation generator to implement single-point or multi-point ablation on the hypertrophic area of the interventricular septum; and
withdrawing the electrode needle from a patient;
wherein the electrode needle enters into the interventricular septum through percutaneous intercostal penetration of a patient's chest, through an epicardium and an apical portion of the interventricular septum.

* * * * *